(12) United States Patent
Miller

(10) Patent No.: US 10,695,544 B2
(45) Date of Patent: *Jun. 30, 2020

(54) INSUFFLATION PUMP

(71) Applicant: Miller Medical LLC, Randolph, NJ (US)

(72) Inventor: Stuart H Miller, Landing, NJ (US)

(73) Assignee: Miller Medical LLC, Randolph, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/146,452

(22) Filed: Sep. 28, 2018

(65) Prior Publication Data

US 2019/0046776 A1 Feb. 14, 2019

Related U.S. Application Data

(63) Continuation of application No. 15/047,054, filed on Feb. 18, 2016, now Pat. No. 10,118,024.

(60) Provisional application No. 62/118,127, filed on Feb. 19, 2015.

(51) Int. Cl.
*A61M 25/10* (2013.01)

(52) U.S. Cl.
CPC .... *A61M 25/10182* (2013.11); *A61M 25/104* (2013.01); *A61M 25/10187* (2013.11)

(58) Field of Classification Search
CPC .......... A61M 25/10182; A61M 25/104; A61M 25/10187; A61B 2017/2941; A61B 17/43; A61B 17/205
USPC .............................................. 604/61, 63, 64
See application file for complete search history.

(56) References Cited

U.S. PATENT DOCUMENTS

| | | | |
|---|---|---|---|
| 1,698,852 A | 1/1929 | Miller et al. | |
| 2,074,401 A | 3/1937 | Kauzal | |
| 2,773,500 A | 12/1956 | Young | |
| 3,669,104 A * | 6/1972 | Wyatt | A61M 37/0069 604/61 |
| 4,472,141 A * | 9/1984 | Dragan | B05C 17/00596 433/90 |
| 4,737,151 A | 4/1988 | Clement et al. | |
| 4,808,165 A | 2/1989 | Carr | |
| 4,976,725 A | 12/1990 | Chin et al. | |
| 5,209,731 A | 5/1993 | Sterman et al. | |
| 5,273,537 A | 12/1993 | Haskvitz et al. | |
| 5,336,201 A | 8/1994 | von der Decken | |
| 5,507,727 A | 4/1996 | Crainich | |
| 5,733,258 A | 3/1998 | Lane | |
| 5,830,194 A | 11/1998 | Anwar et al. | |
| 5,873,499 A | 2/1999 | Leschinsky et al. | |
| 6,030,368 A | 2/2000 | Anwar et al. | |
| 7,041,084 B2 | 5/2006 | Fojtik | |
| 7,306,574 B2 | 12/2007 | Massey et al. | |
| 7,527,605 B2 | 5/2009 | Evans | |

(Continued)

*Primary Examiner* — William R Carpenter
*Assistant Examiner* — Tezita Z Watts
(74) *Attorney, Agent, or Firm* — Welsh Flaxman & Gitler LLC

(57) ABSTRACT

An insufflation pump includes a pump body having a first end and a second end. The pump body includes a syringe mechanism at the first end and an actuation mechanism at the second end. The syringe mechanism includes a plunger. The plunger of the syringe mechanism and the actuation mechanism are linked by a toggle assembly facilitating transfer of power from the actuation mechanism to the syringe mechanism.

18 Claims, 5 Drawing Sheets

(56) References Cited

U.S. PATENT DOCUMENTS

| | | |
|---|---|---|
| 7,534,234 B2 | 5/2009 | Fojtik |
| 8,986,247 B2 | 3/2015 | Miller |
| 2009/0088702 A1 | 4/2009 | Fojtik |
| 2010/0249719 A1* | 9/2010 | Fojtik .................. A61B 5/1405 604/218 |

* cited by examiner

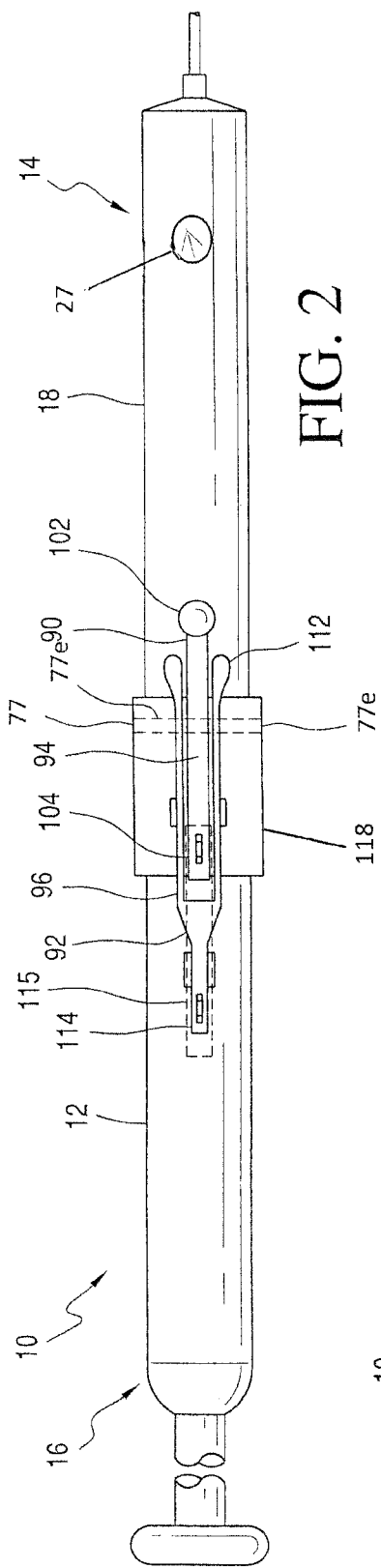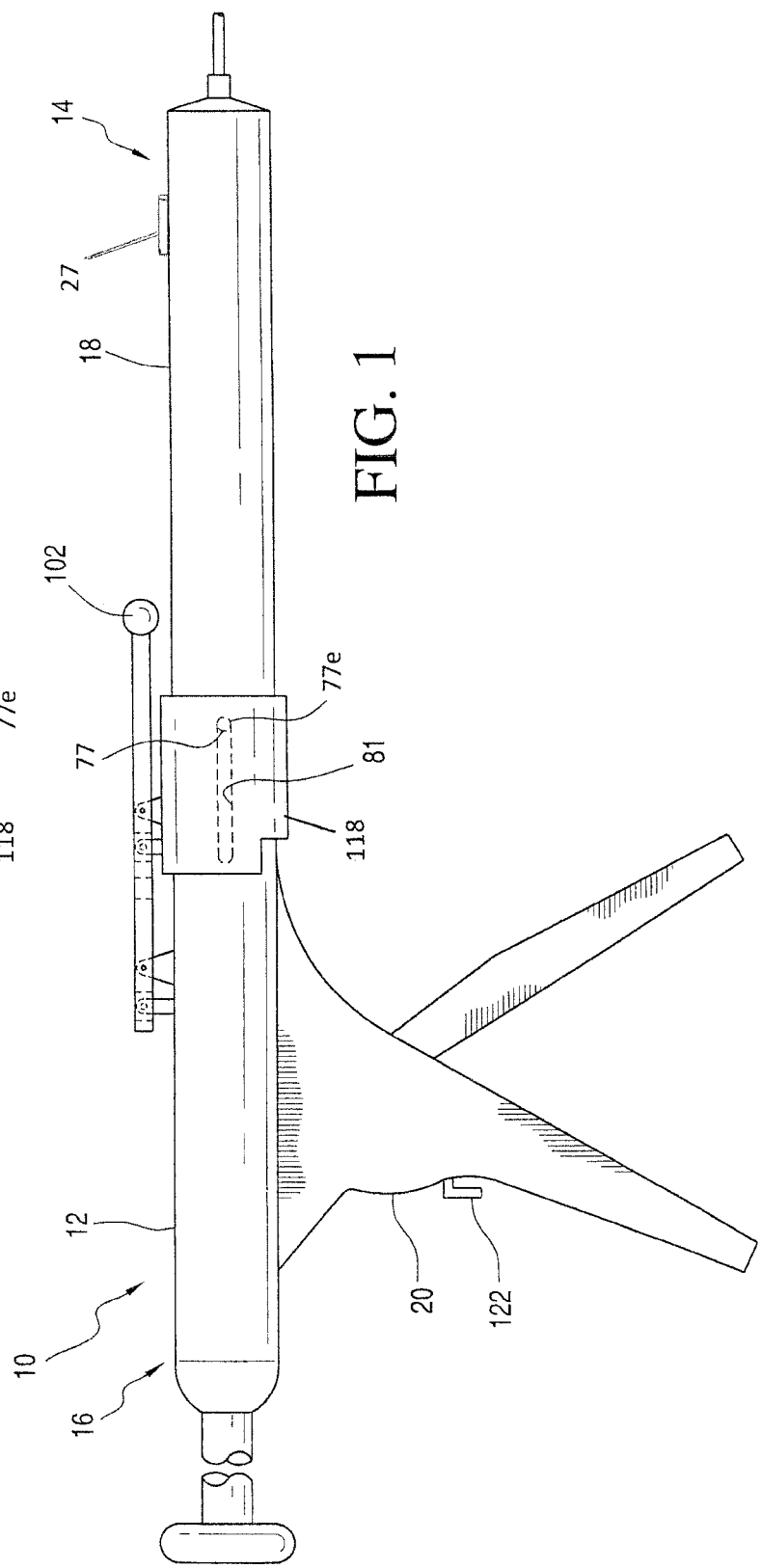

INSUFFLATION PUMP

CROSS REFERENCE TO RELATED APPLICATION

This application is a continuation of U.S. patent application Ser. No. 15/047,054, entitled "INSUFFLATION PUMP," filed Feb. 18, 2016, which claims the benefit of U.S. Provisional Application Ser. No. 62/118,127, entitled "INSUFFLATION PUMP," filed Feb. 19, 2015.

BACKGROUND OF THE INVENTION

1. Field of the Invention

The invention relates to an insufflation pump.

2. Description of the Related Art

Most vascular procedures are now performed in an endovascular fashion; that is, by way of a catheter placed inside of an artery or vein. The benefit of an endovascular, versus a traditional "open", surgical procedure is the greatly decreased morbidity and mortality afforded by the endovascular route, while affording similar overall outcomes. Instead of the traditional surgical bypass procedure performed on the heart, legs, as well as other body parts, endovascular percutaneous transluminal angioplasty, or PTA, is now the standard of care for treating narrowed or blocked arteries and veins. Angioplasty is performed to dilate arteries, veins and other closed, tubular structures within the body. These additional structures may include the biliary tree, ureters, kidneys, as well as other tissue which needs to be expanded radially. Its worldwide acceptance has resulted in millions of PTA, or "angioplasty" procedures performed in the United States and abroad yearly.

When performing angioplasty, the physician advances a specialized catheter, which contains a pre-mounted balloon at its tip, over a guide wire and into the area of abnormal narrowing in the artery or vein. This catheter advancement is accomplished utilizing fluoroscopic guidance, which is essentially a "real time" continuous x-ray image. Once the balloon or angioplasty catheter is precisely placed into the desired area within the blood vessel, the catheter-mounted balloon can be inflated, thusly performing angioplasty within the artery or vein. The inflation of the balloon is accomplished by the use of a device known as an insufflator.

All currently-available insufflators require two hands to inflate the balloon: one to hold the device and one to incrementally increase the fluid forced into the balloon from the insufflator by rotating a threaded screw. A pressure gauge is commonly located on the body of the insufflator so that the balloon can be inflated to a desired atmospheric pressure. The use of an insufflator, as opposed to a simple syringe, results in accurate, reproducible pressures within the angioplasty balloon. Because operation of the insufflator requires two hands, a second physician, or technician, is needed to hold the angioplasty catheter in the proper position during the angioplasty procedure and inflation of the balloon. The primary physician must, therefore, decide which portion of the procedure is most important; that is, controlling inflation rates and pressures in operating the insufflator versus controlling the positioning of the balloon catheter. Not properly positioning the angioplasty balloon may result in damage to a normal portion of the vessel, while not holding the catheter in place could result in undesired movement of the angioplasty balloon, with subsequent traumatic vessel dissection. This results in, as a best-case scenario, inadequate angioplasty due to improper balloon placement, or in the worse scenario, vessel dissection and possible death.

Most recently, with the advent of balloon kyphoplasty for the repair of vertebral compression fractures of the spine, balloon catheters have also been used to expand compressed bone. These procedures similarly require the use of an insufflator in the inflation of the balloon catheter and are consequently beset with the same problems.

Currently, insufflators are filled with a mixture of radiopaque contrast material and sterile saline during a procedure. This mixture allows the angioplasty balloon to be observed under fluoroscopy by the operating physician, and its precise location can be directly observed in real time. In addition, the response of the vessel to angioplasty can be monitored indirectly by viewing the form of the angioplasty balloon using fluoroscopy: a narrow balloon suggests a poorly dilated vessel while a fully expanded balloon suggests a successfully dilated vessel.

With the foregoing in mind, an insufflator adapted for one-handed operation has been developed; as such, it is both held and deployed utilizing one hand as opposed to two. By allowing one hand to be freed, the physician can thusly hold the catheter in its proper position, while controlling both the rate of pressure rise and total pressure achieved by inflation of the angioplasty catheter.

SUMMARY OF THE INVENTION

It is, therefore, an object of the present invention to provide an insufflation pump including a pump body having a first end and a second end. The pump body includes a syringe mechanism at the first end and an actuation mechanism at the second end. The syringe mechanism includes a plunger. The plunger of the syringe mechanism and the actuation mechanism are linked by a toggle assembly facilitating transfer of power from the actuation mechanism to the syringe mechanism.

It is also an object of the present invention to provide an insufflation pump wherein the syringe mechanism includes a syringe barrel and the plunger is positioned within the syringe barrel for movement therein, the syringe barrel is integrally formed with the pump body and includes a distal, first end and a proximal, second end.

It is another object of the present invention to provide an insufflation pump wherein the syringe barrel includes a pressure gauge in communication with an interior of the syringe barrel for measuring applied pressure.

It is a further object of the present invention to provide an insufflation pump wherein the distal, first end of the syringe barrel includes an outlet port through which fluid is dispensed or withdrawn as the plunger moves between the proximal, second end of the syringe barrel of the syringe barrel and the distal, first end of the syringe barrel.

It is also an object of the present invention to provide an insufflation pump wherein the outlet port is shaped and dimensioned for selective attachment of a catheter thereto.

It is another object of the present invention to provide an insufflation pump wherein the plunger includes a plunger shaft having a first end to which a seal member is mounted and a second end which is acted upon by the actuation mechanism.

It is a further object of the present invention to provide an insufflation pump wherein the plunger shaft includes ratchet teeth on an outer surface of the plunger shaft for controlling movement of the plunger shaft in only one direction.

It is also an object of the present invention to provide an insufflation pump wherein the pump body includes an access opening shaped and dimensioned for the passage of the toggle assembly therethrough.

It is another object of the present invention to provide an insufflation pump wherein the actuation mechanism includes a pistol grip having a fixed, handheld lever portion and a spring loaded oscillating lever portion, the toggle assembly being coupled between the oscillating lever portion and the plunger of the syringe assembly.

It is a further object of the present invention to provide an insufflation pump wherein the toggle assembly includes a first linkage member, a second linkage member, a third linkage member and a fourth linkage member.

It is also an object of the present invention to provide an insufflation pump including a push button stop utilized to adjust positioning of the toggle assembly.

It is another object of the present invention to provide an insufflation pump wherein a first end of the first linkage member is fixedly secured to a second end of the oscillating lever portion such that the second end of the first linkage member moves about an arc defined by rotation of the oscillating lever portion, a first end of the second linkage member is pivotally connected to a second end of the first linkage member, a second end of the second linkage member is pivotally connected to both respective second ends of the third and fourth linkage members, and a first end of the fourth linkage member is pivotally secured to the pump body while a first end of the third linkage member is in communication with the plunger for driving the plunger forward as the oscillating lever portion is actuated.

It is a further object of the present invention to provide an insufflation pump wherein the first end of the fourth linkage member is pivotally mounted to the pump body and unable to move along a length of the pump body, and the first end of the third linkage member is caused to move a set distance.

It is also an object of the present invention to provide an insufflation pump wherein a second end of a plunger shaft of the plunger has a channel beam cavity into which the first end of the third linkage member sits for actuation of the plunger shaft along a length of the pump body.

It is another object of the present invention to provide an insufflation pump wherein the first end of the third linkage member is secured to a carriage member having a diametrically oriented guide pin that is secured to the first end of the third linkage member and that passes through the plunger shaft, such that the carriage member engages the plunger shaft via a locking pin during forward motion of the third linkage member and the locking pin disengages from the plunger shaft during rearward motion of the third linkage member and the carriage member.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 1 is a side view of the insufflation pump in accordance with the present invention.

FIG. 2 is a top view of the insufflation pump in accordance with the present invention.

DESCRIPTION OF THE PREFERRED EMBODIMENTS

Figure 3:
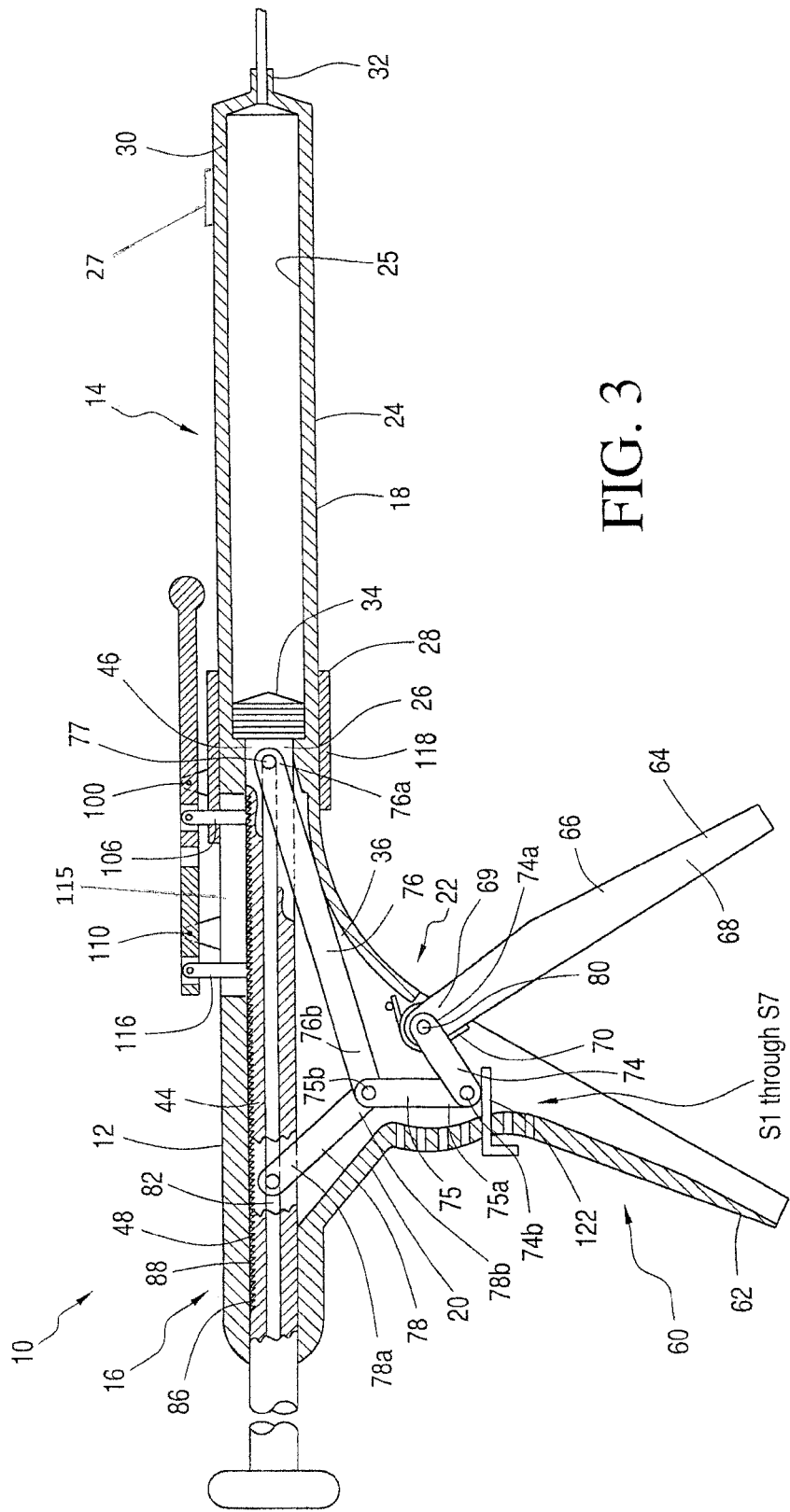
FIG. 3 is a cross sectional view of the insufflation pump.
Figure 4:
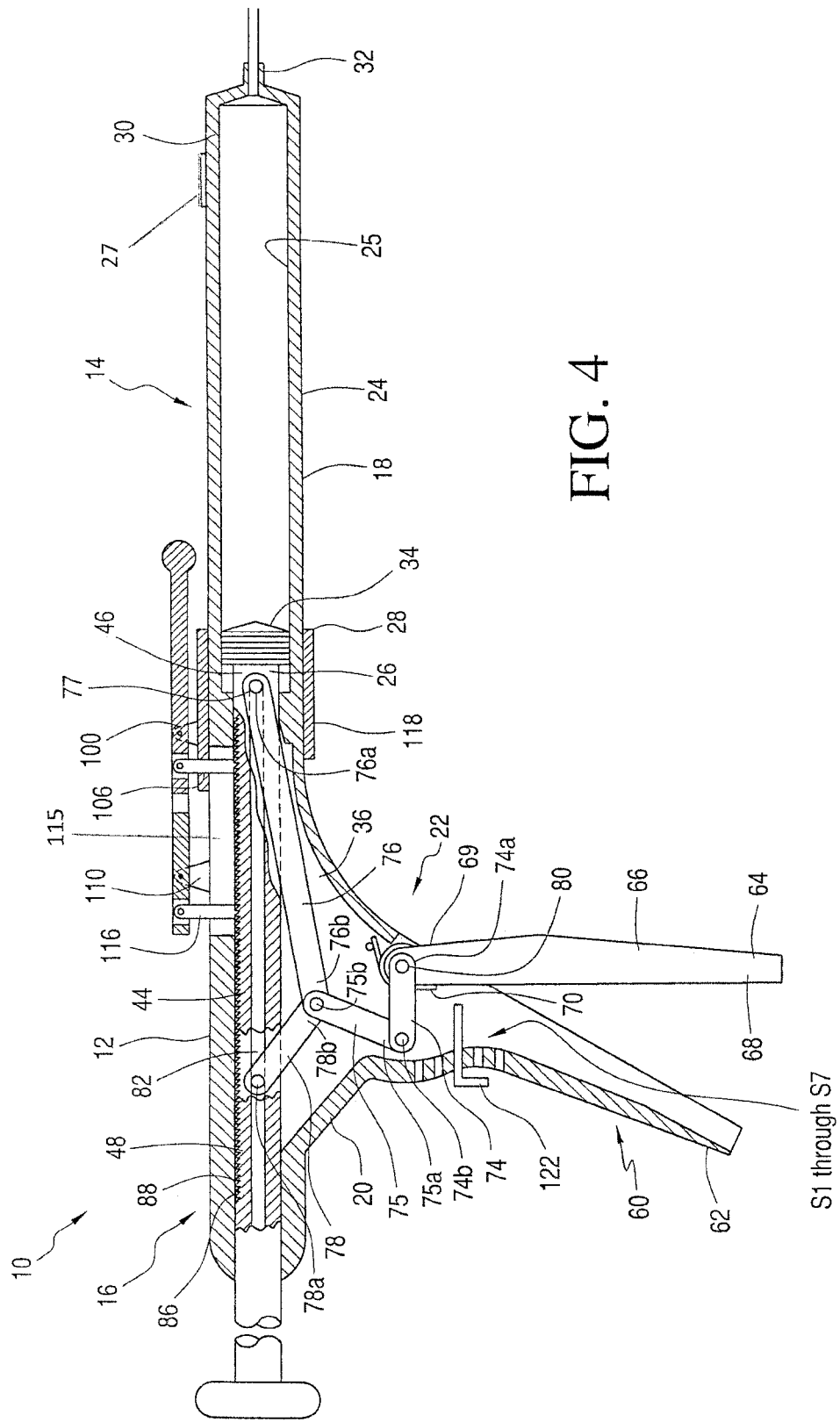
FIGS. 4-6 are cross sectional views showing the insufflation pump in various stages of use.
Figure 5:
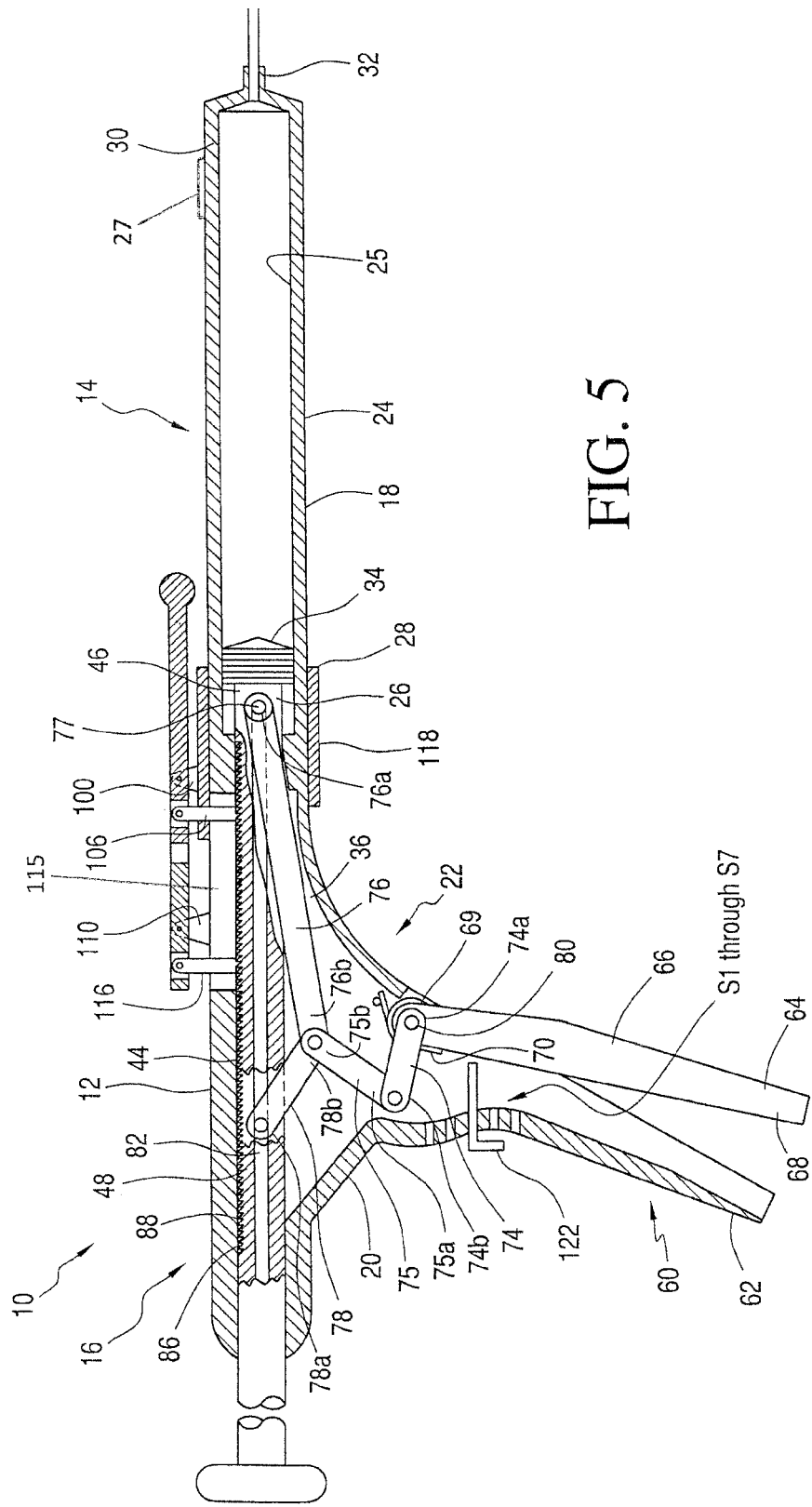
Figure 6:
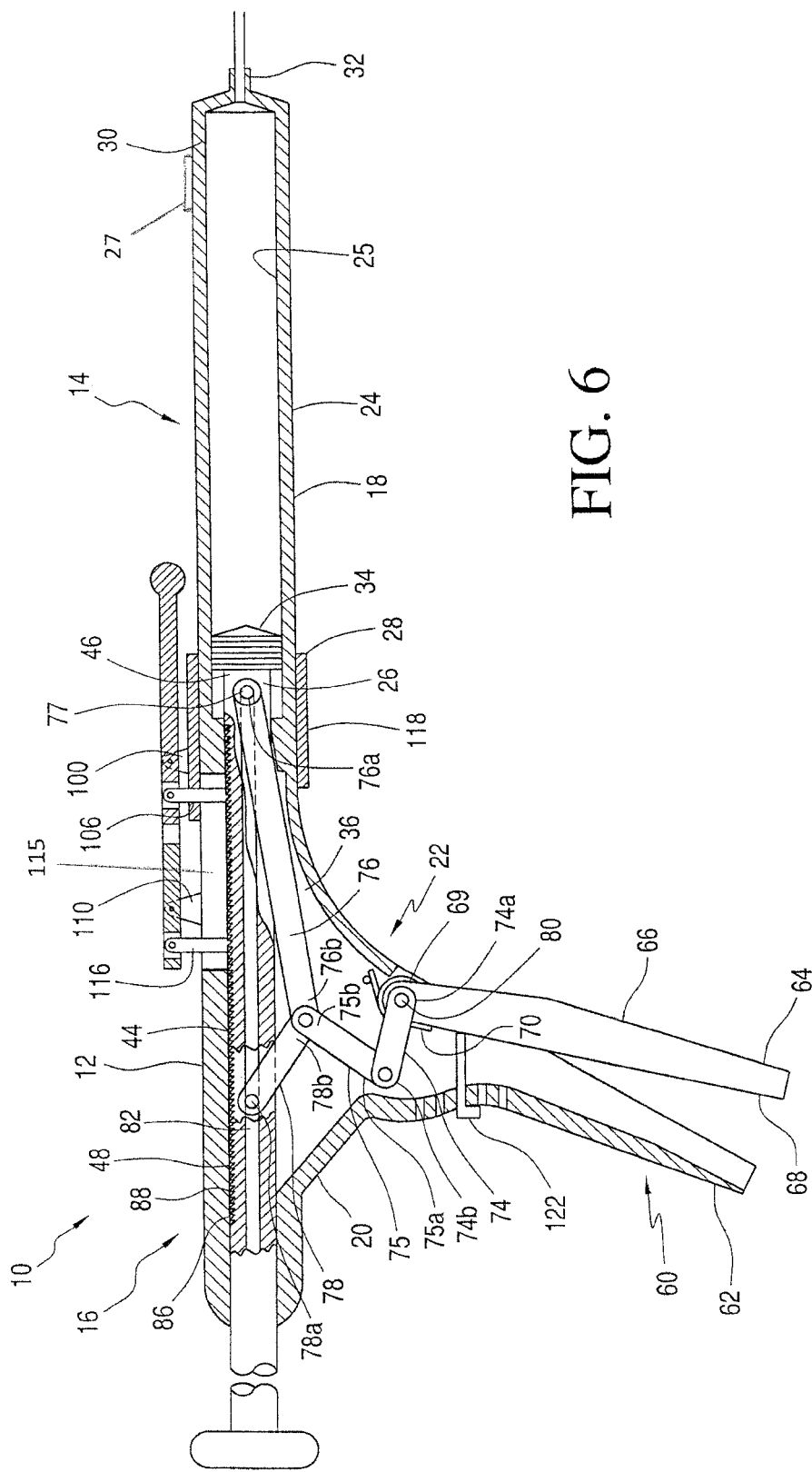

The detailed embodiments of the present invention are disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 6, an insufflation pump 10 is disclosed. The insufflation pump 10 allows for single handed actuation for inflation of dilatation balloons and other inflatable devices employed during medical procedures.

The insufflation pump 10 includes a pump body 12 having a first end 14 and a second end 16. The first end 14 is provided with a syringe mechanism 18 and the second end 16 is provided with an actuation mechanism 20. The syringe mechanism 18 and the actuation mechanism 20 are linked by a toggle assembly 22 facilitating the transfer of power from the actuation mechanism 20 to the syringe mechanism 18.

The insufflation pump 10 includes a plunger 26 of a syringe mechanism 18 attached to a lever system, composed of the actuation mechanism 20 and toggle assembly 22, which greatly amplifies the mechanical advantage necessary to create the large atmospheric pressures needed for adequate catheter balloon inflation. Once filled with radiopaque contrast and saline, the entire angioplasty process may be performed by a single physician. One hand holds the angioplasty catheter while the other hand is used to activate the insufflation pump 10 of the present invention. In this manner, a more precise, controlled angioplasty may be performed since one person controls both the placement as well as the inflation of the balloon.

First considering the syringe mechanism 18 at the first end 14 of the pump body 12, the syringe mechanism 18 includes a syringe barrel 24 and a plunger 26 positioned within the syringe barrel 24 for movement therein. The syringe barrel 24 is integrally formed with the pump body 12 and includes a proximal, second end 28 and a distal, first end 30. The syringe barrel 24 also includes a pressure gauge 27 in communication with the interior of the syringe barrel 24 for measuring applied pressure. The proximal, second end 28 is closed by the plunger 26 while the distal, first end 30 includes an outlet port 32 through which fluid is dispensed or withdrawn as the plunger 26 moves between the proximal, second end 28 of the syringe barrel 24 and the distal, first end 30 of the syringe barrel 24. The outlet port 32 is shaped and dimensioned for selective attachment of a catheter to the syringe barrel 24 for the transfer of fluid to and from the syringe barrel 24, that is, between the dilatation catheter and the syringe mechanism 18. The outlet port 32 at the distal, first end 30 of syringe barrel 24 is closed by the seal member 34 of plunger 26 when the piston is in its fully extended position adjacent the distal, first end 30.

The creation of a sealed environment within the syringe barrel 24, in particular, between the outlet port 32 and the plunger 26, is achieved by the provision of a seal member 34 about the circumference of the plunger 26. In particular, the plunger 26 includes a plunger shaft 44 having a first end 46 to which the seal member 34 is mounted and a second end 48 which is acted upon by the actuation mechanism 20 in the manner discussed below in greater detail. The seal member 34 is shaped and dimensioned to engage the inner wall 25 of the syringe barrel 24. As such, fluid is prevented from escaping distally of the plunger 26 as it moves within the syringe barrel 24. In addition, and when the outlet port 32 is connected to a dilatation catheter, a closed system is achieved wherein fluid may move between the syringe barrel 24 and the dilatation catheter but will not escape the confines of the syringe barrel 24 and dilatation catheter. Consequently, when the plunger 26 moves toward the outlet port 32, fluid is forced out of the syringe barrel 24 and into the dilatation catheter. When the plunger 26 is moved distally away from the outlet port 32, a vacuum is formed drawing fluid from the dilatation catheter back into the syringe barrel 24.

As will be appreciated after reading the following disclosure regarding the actuation mechanism 20, the pump body 12 is provided with an access opening 36 for the toggle assembly 22, that is, the access opening 36 is shaped and dimensioned for the passage of the toggle assembly 22 therethrough. The access opening 36 is sealed from fluid communication with the fluid being moved between the syringe barrel 24 and the dilatation catheter by the provision of the seal member 34 about the circumference of the plunger 26. The seal member 34 of the plunger 26 creates a barrier separating the access opening 36 from the fluid and allowing the syringe mechanism 18 to maintain a closed system while permitting the actuation mechanism 20 to link with the plunger 26 for causing movement thereof.

With regard to the actuation mechanism 20, it includes a pistol grip 60 having a fixed, handheld lever portion 62 and a spring loaded oscillating lever portion 64. Movement of the pivoted, oscillating lever portion 64 from its rest configuration (with the fixed, handheld lever portion 62 and the spring 70 loaded oscillating lever portion 64 spaced from each other as shown in FIG. 3) forces the plunger 26 and the plunger shaft 44 to move to the right down the syringe barrel 24 of the syringe mechanism 18. This increases the pressure on the saline in the syringe barrel 24.

More particularly, the oscillating lever portion 64 includes a handle 66 having a free first end 68 for engagement by the hand of an operator and a second end 69 pivotally secured to the fixed handheld lever portion 62. The lever portion 64 is mechanically coupled to the toggle assembly 22 for generating movement of the plunger 26 as the oscillating lever portion 64 is repeatedly compressed and released.

The toggle assembly 22 includes a first linkage member 74, a second linkage member 75, a third linkage member 76 and a fourth linkage member 78. Each of the first linkage member 74, the second linkage member 75, the third linkage member 76 and the fourth linkage member 78 includes a first end 74a, 75a, 76a, 78a and a second end 74b, 75b, 76b, 78b. With this in mind, the first end 74a of the first linkage member 74 is fixedly secured to the second end 69 of the oscillating lever portion 64 such that the second end 74b of the first linkage member 74 moves about an arc defined by the rotation of the oscillating lever portion 64 at the pivot point 80. In accordance with a preferred embodiment the oscillating lever portion 64 and the first linkage member 74 are found as a single piece, although it is appreciated they may be found as separate pieces that are fixedly connected.

The second linkage member 75 is pivotally secured between the first linkage member 74 and the third and fourth linkage members 76, 78. In particular, the first end 75a of the second linkage member 75 is pivotally connected to the second end 74b of the first linkage member 74. The second end 75b of the second linkage member 75 is pivotally connected to both the second ends 76b, 78b of the third and fourth linkage members 76, 78. The respective second ends 76b, 78b of the third linkage member 76 and the fourth linkage member 78 are pivotally secured to the second end 75b of the second linkage member 75 such that the second, third and fourth linkage members 75, 76, 78 pivot about the same axis. The first end 78a of the fourth linkage member 78 is pivotally secured to the pump body 12 of the insufflation pump 10 while the first end 76a of the third linkage member 76 is in communication with the plunger shaft 44 of the plunger 26 for driving the plunger shaft 44 forward as the oscillating lever portion 64 is actuated in accordance with the present invention.

In practice, the geometry of the oscillating lever portion 64 and the first linkage member 74 forces the second end 74b of the first linkage member 74 to follow a circular path at the end of first linkage member 74 as the oscillating lever portion 64 moves through its pivoting motion relative to the handheld lever portion 62. This movement causes forced movement of the second linkage member 75 that ultimately results in forced movement of the second ends 76b, 78b of the third and fourth linkage members 76, 78. Because the first end 78a of the fourth linkage member 78 is pivotally mounted to the pump body 12 of the insufflation pump 10 (and is therefore unable to move along the length of the pump body 12), the first end 76a of the third linkage member 76 is caused to move a set distance (see FIGS. 3, 4 and 5). In accordance with a preferred embodiment, the set distance is approximately ½ inch. It is appreciated this distance may be adjusted by varying the lengths of the various linkage members.

The second end 48 of the plunger shaft 44 of the plunger 26 has a channel beam cavity 82 into which the first end 76a of the third linkage member 76 sits for actuation of the plunger shaft 44 along the length of the pump body 12 (and particularly toward the second end of the syringe barrel 24). More particular, as the oscillating lever portion 64 is moved toward the fixed, handheld lever portion 62 (see FIGS. 3-6), the first end 76a of the third linkage member 76 is moved in a direction toward the distal, first end 30 of the syringe barrel 24. As a result of interaction between the first end 76a of the third linkage member 76 and the channel beam cavity 82 of the plunger shaft 44, the movement of the first end 76a of the third linkage member 76 is transferred to the plunger shaft 44 causing movement of the plunger 26 toward the distal, first end 30 of the syringe barrel 24.

More particularly, the first end 76a of the third linkage member 76 is secured to a carriage member 118 having a diametrically oriented guide pin 77 that is secured to the first end 76a of the third linkage member 76 and that passes through the plunger shaft 44. The carriage member 118 engages the plunger shaft 44 via a locking pin 106 (discussed below) during forward motion (that is, toward the distal, first end 30 of the syringe barrel 24) of the third linkage member 76 and the locking pin 106 disengages from the plunger shaft 44 during rearward motion of the third linkage member 76 and the carriage member 118. As such, when the oscillating lever portion 64 is compressed, the first linkage member 74, the second linkage member 75, the third linkage member 76 and the fourth linkage member 78 move in a manner causing the first end 76a of the third linkage member 76 to move toward the distal, first end 30 of the syringe barrel 24. During this distal motion, the carriage member 118 is moved forward and, with the locking pin 106 of the carriage member 118 engaging the plunger shaft 44, the plunger shaft 44 is forced in a direction toward the distal, first end 30 of the syringe barrel 24.

Once movement of the oscillating lever portion 64 is completed, that is, the compression cycle is completed, the oscillating lever portion 64 of the pistol grip 60 is released and the spring 70 bias in the oscillating lever portion 64 causes the oscillating lever portion 64 to move to the released orientation. During this movement from the fully compressed orientation to the released orientation, the first linkage member 74, the second linkage member 75, the third linkage member 76 and the fourth linkage member 78 move in a manner causing the first end 76a of the third linkage member 76 to move away from the distal, first end 30 of the syringe barrel 24. During this motion, the carriage member 118 moves rearwardly in the same direction as the first end 76a of the third linkage member 76 and the locking pin 106 of the carriage member 118 disengages from the plunger shaft 44 in a manner allowing the carriage member to move rearwardly without causing the plunger shaft 44 to move rearwardly. As is explained below in greater detail, the engagement and disengagement of the locking pin with the plunger shaft is a result of the relative orientation of the ratchet teeth 86 and the shape of the end of the locking pin 106 which contact the ratchet teeth 86.

Movement of the carriage member 118 is controlled by the guide pin 77 pivotally connected to the first end 76a of the third linkage member 76. In addition to providing for a pivotal connection between the first end 76a of the third linkage member 76 and the carriage member 118, ends 77e of the guide pin 77 extend through slots 81 formed in the housing of the pump body 12 to seat within opposite sides of the carriage member 118 so as to link the carriage member 118 with the first end 76a of the third linkage member 76 to control the back and forth movement thereof.

As briefly mentioned above, controlled movement of the plunger shaft 44 in only one direction, that is, toward the distal end of the syringe barrel 24 is achieved by the provision of ratchet teeth 86 on the outer surface 88 of the plunger shaft 44. The ratchet teeth 86 are shaped and dimensioned for engagement with the locking pin of a toggle control assembly 90 that selectively limits movement of the plunger shaft 44 by selectively engaging the ratchet teeth 86. As such, and with the locking pin 106 of the toggle control assembly 90 engaging the ratchet teeth 86 in a manner allowing for forward movement of the plunger shaft 44 with the forward movement of the toggle control assembly 90, compression of the oscillating lever portion 64 causes forward movement of the first end 76a of the third linkage member 76 which (through the interaction of the toggle locking pin 106 of the carriage member 118 with the plunger shaft 44) moves the plunger shaft 44 forward toward the distal, first end 30 of the syringe barrel 24. Upon release of the oscillating lever portion 64, it rotates away from the fixed, handheld lever portion 62 causing the first end 76a of the third linkage member 76 to move rearwardly. Because the toggle locking pin 106 of the carriage member 118 at the first end 76a of the third linkage member 76 and the ratchet teeth 86 are shaped to not engage when the locking pin 106 is moved in a rearward direction relative to the plunger shaft 44, the carriage member 118 (along with the locking pin 106 and the toggle control assembly 90) move rearwardly while the plunger shaft 44 remains stationary, and the oscillating lever portion 64 is ready for another cycle.

In accordance with a preferred embodiment, the portion of the plunger shaft 44 diametrically and symmetrically below the ratchet teeth 86 contains an axial slot through which the third and fourth linkage members 76, 78 enter and leave the plunger shaft 44. The entire plunger shaft 44 is slip fit in the pump body 12 of the insufflation pump 10. This feature allows the plunger shaft 44 to be radially supported over its entire length. This feature reinforces the plunger shaft 44 so that it does not deflect excessively in a direction perpendicular to the longitudinal axis of the plunger shaft 44.

As briefly discussed above, a toggle control assembly 90 is provided. In addition, the insufflation pump 10 includes a piston control assembly 92. The toggle control assembly 90 and piston control assembly 92 are designed so that the plunger shaft 44 may be driven down the entire length of the syringe barrel 24 in one motion or in varying increments up to ½ inch for the present insufflation pump 10. Moving the plunger 26 the entire length of the syringe barrel 24 permits the physician to fill the syringe barrel 24 with saline by merely depressing the toggle and piston control levers 94, 96 at the same time and pulling the plunger shaft 44 to the left (as shown in FIGS. 1-6). Emptying of the syringe mechanism 18 is achieved by pushing the end of the plunger shaft 44 while the piston control lever 96 is depressed (as the toggle control lever 94 provides for movement of the plunger shaft 44 toward the proximal, second end 30 of the syringe barrel 24 as discussed above). These two procedures are very helpful in removing any trapped air in the saline.

Both the toggle control assembly 90 and piston control assembly 92 rely upon spring biased lever mechanisms to selectively bring a locking pin 106, 116 into contact with the ratchet teeth 86 of the plunger shaft 44. The toggle control assembly 90 is part of the carriage member 118 and, therefore, moves with the carriage member 118 as it is driven forward and backward on the control of the toggle assembly 22. The toggle control assembly 90 includes a spring biased toggle lever arm 94 pivotally mounted upon a pivot projection 100 secured to the carriage member 118 that is wrapped about the barrel 24 for movement relative thereto. The toggle lever arm 94 includes a handle first end 102 positioned on one side of the pivot projection 100 and an actuation second end 104 positioned on the opposite side of the pivot projection 100. The toggle locking pin 106 extends downwardly from the second end 104 such that it may be brought into and out of engagement with the ratchet teeth 86 of the plunger shaft 44 to control the incremental forward motion of the plunger 26. As discussed above, the ratchet teeth 86 and the end of the toggle locking pin 106 are shaped such that they engage when the locking pin 106 is moved in a forward direction toward the first end 30 of the syringe barrel 24 so as to cause movement of the plunger shaft 44 in this direction. The ratchet teeth 86 and the end of the toggle locking pin 106 are further shaped to prevent engagement and allow relative movement between the toggle locking pin 106 and the plunger shaft 44 when the locking pin 106 is moved in a rearward direction away from the first end 30 of the syringe barrel 24 so as to allow movement of the carriage member while also allowing the plunger shaft 44 to remain in its position.

The piston control assembly 92 includes a spring biased plunger lever arm 96 pivotally mounted upon a pivot projection 110 secured to the pump body 12. The plunger lever arm 96 includes a handle first end 112 positioned on one side of the pivot projection 110 and an actuation second end 114 positioned on the opposite side of the pivot projection 110. The plunger locking pin 116 extends downwardly from the second end 114 such that it may be brought into and out of engagement with the ratchet teeth 86 of the plunger shaft 44 to control the rearward motion of the plunger 26 when it is time to fill the syringe. The ratchet teeth 86 and the end of the plunger locking pin 116 are shaped such that they engage/disengage in opposite directions relative to the toggle locking pin 106. In particular, the ratchet teeth 86 and the end of the plunger locking pin 116 are shaped to engage when the plunger shaft 44 is moved in a rearward direction away from the distal, first end 30 of the syringe barrel 24 so as to prevent undesired rearward motion. Because the piston control assembly 92 is fixedly secured to the pump body 12 this prevents rearward movement of the plunger shaft 44 unless the piston control assembly 92 is actuated to move the plunger locking pin 116 away from the ratchet teeth 86 of the plunger shaft 44. The ratchet teeth 86 and the end of the plunger locking pin 116 are further shaped to prevent engagement and allow relative movement between the plunger locking pin 116 and the plunger shaft 44 when the plunger shaft 44 is moved in a forward direction toward the distal, first end 30 of the syringe barrel 24 (for example, upon actuation of the toggle assembly 22).

Access of the toggle locking pin 106 and the plunger locking pin 116 to the ratchet teeth 86 of the plunger shaft 44 is facilitated by the provision of a slot 115 in the housing through which the toggle locking pin 106 and the plunger locking pin 116 pass. As discussed above, the toggle control assembly 90 is mounted upon a cylindrical slide 118, in the form of a circular ring portion, which is slip fit over the outer diameter of the syringe barrel 24 for movement relative thereto.

In accordance with a preferred embodiment, the pistol grip 60 employed in accordance with the present configuration is used to increase the pressure on the saline maintained within the syringe mechanism 18. Repetitive squeezing and releasing of the pistol grip 60 drives the plunger 26 incrementally to the right down the entire length of the barrel thereby increasing the pressure on the saline to a desired level.

If the saline pressure has to be raised or lowered for some reason, the position of the pistol grip push button stop 122 should be adjusted. The push button stop 122 is utilized to adjust the positioning of the linkage members. For example, if the hand force required to operate the pistol grip 60 is excessively high and difficult to use, the user may move the push button stop 122 to another slot S-1 through S-7 on the handheld lever portion 62 so as to lower the linkage angles. If the hand force is too low, the user may move the push button stop 12 to increase the linkage angles.

More particularly, controlled application of the applied pressure level is achieved by moving the push button stop 122 amongst slots S-1 through S-7 found in the housing of the pump body 12 along the handheld lever portion 62 at the various pistol grip push button locations. The slots S-1 through S-7 control the ability of the pistol grip 60 to move through an actuation cycle. More particularly, the push button stop 122 is selectively inserted and removed from the slots S-1 through S-7 so as to adjust applied pressure levels. For example, if a medical practitioner is working at the level of slot 4 (S-4) and the medical practitioner wants to increase the pressure level to a higher value, the medical practitioner may simply actuate the pistol grip 60, pull the push button stop 122 from slot 4 (S-4), increase the pressure on the pistol grip 60 and insert the push button stop 122 into slot 5 (S-5).

Where the user desires to decrease the applied pressure level, for example, from the pressure level achieved at slot 4 (S-4) to the pressure level achieved at slot 3 (S-3), the medical practitioner will activate the pistol grip 60 for the first half of its cycle and hold it there. At this point, the medical practitioner will remove the push button stop 122 from slot 4 (S-4) and move the push button stop 122 into slot 3 (S-3). Thereafter, the medical practitioner will activate the piston and toggle control assemblies 90, 92 to allow the plunger 26 to move backward. Thereafter, the medical practitioner will gradually lower the hand load on the pistol grip 60 to allow the piston pressure loading to be lowered.

It should be remembered that the toggle control assembly 90 and piston control assembly 92 hold the plunger 26 in place as discussed above. As such, one must continue to hold the pistol grip 60 at the pressure level of slot 4 (S-4) for the first half of its cycle before operating the toggle control assembly 90 and piston control assembly 92. Once toggle control assembly 90 and piston control assembly 92 are released, the medical practitioner may then gradually release the hand force on the pistol grip 60 to lower the pressure from the level at slot 4 (S-4) to the level at slot 3 (S-3) in a gradual manner. The medical practitioner must be sure to maintain a suitably high hand load on the pistol grip 60 to be sure the medical practitioner is operating the plunger 26, the toggle control assembly 90 and the piston control assembly 92, because during such motion the plunger 26 will be free to travel backwards as the syringe loadings are up to 20 atmospheres under the toggle control assembly 90 and piston control assembly 92. As such, the medical practitioner must hold the pistol grip 60 with a hand load as high as that used to remove the push button stop 122 from slot 4 (S-4) because the backward motion of the plunger 26 will be driven by the pressure on the plunger 26. Control of the pressure on the plunger 26 is achieved by gradually lowering the pressure on it using the hand operated pistol grip 60.

In an effort to ensure operability of the present invention, a mathematical analysis was conducted on a model of the insufflation pump 10 as shown herein. The model simulated the use of the toggle control assembly 90 and piston control assembly 92 using ten iterations of the angles involved. For example, the objective of the test was to inflate the balloon to 20 atmospheres of pressure and transfer 20 ml of saline into and out of the balloon. With this in mind, the respective control levers of the toggle control assembly 90 and piston control assembly 92 were held down so as to enable the plunger 26 to be fully displaced to the right and left by pushing directly on the plunger shaft 44. To fill the insufflation pump 10 with saline, for example, the medical practitioner holds down the respective levers of the toggle control assembly 90 and piston control assembly 92 and draws saline into the insufflation pump 10 by pulling the plunger shaft 44 to the left. The end of the insufflation pump 10, of course, is submerged in a supply of saline. Any air bubbles in the insufflation pump 10 may be removed by displacing the piston forward and backward until all of the air bubbles are removed.

It should be noted, in an alternate embodiment, that the syringe end of the insufflation pump 10 may be made with an attachment member such that 5 ml saline cartridges (for example) may be loaded into the insufflation pump 10 by merely depressing the actuator and drawing the plunger to its maximum retracted position. Depressing the actuator will then discharge the fluid from the cartridge into attached tubing preferably secured thereto via a luer lock.

The present insufflation pump 10 may also be employed for easy and accurate catheter flushing that, in many cases, can be easily accomplished by nurses, nurses' aides, and even the patient in many instances. The insufflation pump 10 is a small, sterile, prefilled device for single use that can be easily placed and deployed. The insufflation pump 10 is removed from the package and a small amount of saline is discharged using the actuator. After wiping with a sterile wipe, the insufflation pump 10 is connected to the catheter. A small amount of fluid residing in the catheter is then withdrawn from the catheter. Any air bubbles should be removed using current techniques. On the down stroke motion of the actuator, the sterile saline in the insufflation pump 10 is forward flushed into the balloon portion of the catheter. The device is then removed and discarded.

It is appreciated the insufflation pump 10 may be molded, for example, from General Electric HP or any other plastic suitable for medical devices. The enclosed drawings show an "O" ring seal on the piston. This was selected for prototyping purposes and may be replaced by conventional syringe piston seals.

The insufflation pump 10 described herein can be used as a relatively low pressure flushing device. With some modifications, such as the addition of a pressure gauge and overall strengthening of the structure, the basic flusher concept may also be used to inflate balloons.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An insufflation pump, comprising:
   a pump body having a first end and a second end;
   the pump body includes a syringe mechanism at the first end and an actuation mechanism at the second end, the syringe mechanism including a plunger, the syringe mechanism includes a syringe barrel and the plunger is positioned within the syringe barrel for movement therein, the syringe barrel is integrally formed with the pump body and includes a proximal, second end and a distal, first end, and the actuation mechanism includes a pistol grip having a fixed, handheld lever portion and a spring loaded oscillating lever portion;
   wherein the plunger of the syringe mechanism and the actuation mechanism are linked by a toggle assembly coupled between the spring loaded oscillating lever portion and the plunger of the syringe assembly, the toggle assembly facilitating transfer of power from the actuation mechanism to the syringe mechanism, the toggle assembly is composed of a plurality of linkage members driving the plunger forward as the spring loaded oscillating lever portion is actuated, the toggle assembly is secured to a carriage member having a diametrically oriented guide pin that is secured to the toggle assembly and that passes through a plunger shaft of the plunger, such that the carriage member engages the plunger shaft via a locking pin during forward motion of the toggle assembly and the locking pin disengages from the plunger shaft during rearward motion of the toggle assembly and the carriage member.

2. The insufflation pump according to claim 1, wherein the syringe barrel includes a pressure gauge in communication with an interior of the syringe barrel for measuring applied pressure.

3. The insufflation pump according to claim 1, wherein the distal, first end of the syringe barrel includes an outlet port through which fluid is dispensed or withdrawn as the plunger moves between the proximal, second end of the syringe barrel and the distal, first end of the syringe barrel.

4. The insufflation pump according to claim 3, wherein the outlet port is shaped and dimensioned for selective attachment of a catheter thereto.

5. The insufflation pump according to claim 1, wherein the the plunger shaft includes a first end to which a seal member is mounted and a second end which is acted upon by the actuation mechanism.

6. The insufflation pump according to claim 5, wherein the plunger shaft includes ratchet teeth on an outer surface of the plunger shaft for controlling movement of the plunger shaft in only one direction.

7. The insufflation pump according to claim 1, wherein the pump body includes an access opening shaped and dimensioned for the passage of the toggle assembly therethrough.

8. The insufflation pump according to claim 1, wherein the toggle assembly includes a first linkage member, a second linkage member, a third linkage member and a fourth linkage member.

9. The insufflation pump according to claim 8, further including a push button stop utilized to adjust positioning of the toggle assembly.

10. The insufflation pump according to claim 8, wherein a first end of the first linkage member is fixedly secured to a second end of the oscillating lever portion such that the second end of the first linkage member moves about an arc defined by rotation of the spring loaded oscillating lever portion, a first end of the second linkage member is pivotally connected to a second end of the first linkage member, a second end of the second linkage member is pivotally connected, respectively, to both a second end of the third linkage member and a second end of the fourth linkage member and a first end of the fourth linkage member is pivotally secured to the pump body while a first end of the third linkage member is in communication with the plunger for driving the plunger forward as the oscillating lever portion is actuated.

11. The insufflation pump according to claim 10, wherein the first end of the fourth linkage member is pivotally mounted to the pump body and unable to move along a length of the pump body, and the first end of the third linkage member is caused to move a set distance.

12. The insufflation pump according to claim 10, wherein the second end of the plunger shaft has a channel beam cavity into which the first end of the third linkage member sits for actuation of the plunger shaft along a length of the pump body.

13. The insufflation pump according to claim 12, wherein the first end of the third linkage member is secured to the carriage member and the diametrically oriented guide pin is secured to the first end of the third linkage member and passes through the plunger shaft, such that the carriage member engages the plunger shaft via the locking pin during forward motion of the third linkage member and the locking pin disengages from the plunger shaft during rearward motion of the third linkage member and the carriage member.

14. The insufflation pump according to claim 1, further including a push button stop utilized to adjust positioning of the toggle assembly.

15. The insufflation pump according to claim 1, further including a toggle control assembly and a piston control assembly.

16. The insufflation pump according to claim 1, further including a toggle control assembly and a piston control assembly.

17. An insufflation pump, comprising:
   a pump body having a first end and a second end;
   the pump body includes a syringe mechanism at the first end and an actuation mechanism at the second end, the syringe mechanism including a plunger, the syringe mechanism includes a syringe barrel and the plunger is positioned within the syringe barrel for movement therein, the syringe barrel is integrally formed with the pump body and includes a proximal, second end and a distal, first end, and the actuation mechanism includes a pistol grip having a fixed, handheld lever portion and a spring loaded oscillating lever portion;

wherein the plunger of the syringe mechanism and the actuation mechanism are linked by a toggle assembly coupled between the spring loaded oscillating lever portion and the plunger of the syringe assembly, the toggle assembly facilitating transfer of power from the actuation mechanism to the syringe mechanism, the toggle assembly is composed of a first linkage member, a second linkage member, a third linkage member and a fourth linkage member, wherein a first end of the first linkage member is fixedly secured to a second end of the spring loaded oscillating lever portion such that the second end of the first linkage member moves about an arc defined by rotation of the spring loaded oscillating lever portion, a first end of the second linkage member is pivotally connected to a second end of the first linkage member, a second end of the second linkage member is pivotally connected, respectively, to both a second end of the third linkage member and a second end of the fourth linkage member, and a first end of the fourth linkage member is pivotally secured to the pump body while a first end of the third linkage member is in communication with the plunger for driving the plunger forward as the spring loaded oscillating lever portion is actuated, wherein the toggle assembly is secured to a carriage member having a guide pin allowing for the carriage member to engage and disengage a plunger shaft in a manner causing movement of the plunger shaft.

18. The insufflation pump according to claim 17, wherein the first end of the third linkage member is secured to the guide pin of the carriage member and guide pin passes through the plunger shaft, such that the carriage member engages the plunger shaft via a locking pin during forward motion of the third linkage member and the locking pin disengages from the plunger shaft during rearward motion of the third linkage member and the carriage member.

* * * * *